(12) United States Patent
Dennis

(10) Patent No.: US 7,862,571 B2
(45) Date of Patent: Jan. 4, 2011

(54) OCCLUSION CLIP AND METHOD OF APPLYING SAME

(75) Inventor: William G. Dennis, Jacksonville, FL (US)

(73) Assignee: Microline Surgical, Inc., Beverly, MA (US)

( * ) Notice: Subject to any disclaimer, the term of this patent is extended or adjusted under 35 U.S.C. 154(b) by 1237 days.

(21) Appl. No.: 10/626,966

(22) Filed: Jul. 25, 2003

(65) Prior Publication Data

US 2005/0021061 A1    Jan. 27, 2005

(51) Int. Cl.
*A61B 17/10* (2006.01)
(52) U.S. Cl. .............................. 606/143; 606/157
(58) Field of Classification Search .............. 606/138, 606/139, 142, 143, 151, 157, 158, 144, 145, 606/146, 147, 148, 152, 153
See application file for complete search history.

(56) References Cited

U.S. PATENT DOCUMENTS

| | | | |
|---|---|---|---|
| 4,274,415 | A | 6/1981 | Kanamoto et al. |
| 4,325,377 | A | 4/1982 | Boebel |
| 4,556,060 | A | 12/1985 | Perlin |
| 4,658,822 | A | 4/1987 | Kees, Jr. |
| 4,966,603 | A | 10/1990 | Focelle et al. |
| 4,976,722 | A | 12/1990 | Failla |
| 4,979,950 | A | 12/1990 | Transue et al. |
| 5,030,226 | A | 7/1991 | Green et al. |
| 5,063,045 | A | 11/1991 | Namimatsu et al. |
| 5,156,609 | A | 10/1992 | Nakao et al. |
| 5,303,226 | A | 4/1994 | Okanoue et al. |
| 5,312,426 | A | 5/1994 | Segawa et al. |
| 5,342,373 | A | 8/1994 | Stefanchik et al. |

(Continued)

FOREIGN PATENT DOCUMENTS

DE    3238892    4/1984

(Continued)

OTHER PUBLICATIONS

International Search Report for PCT/US2004/023270.

(Continued)

*Primary Examiner*—Anhtuan T Nguyen
*Assistant Examiner*—Tuan V Nguyen
(74) *Attorney, Agent, or Firm*—Greenblum & Bernstein, P.L.C.

(57) ABSTRACT

An occlusion clip is disclosed that comprises an upper occlusion member having substantially parallel first and second upper occlusion arms each having proximal and distal upper occlusion arm ends. The first and second upper occlusion arms define an upper main body width dimension. An upper arcuate portion connects the first and second upper occlusion arms at their distal ends. The occlusion clip also comprises a lower occlusion member having substantially parallel first and second lower occlusion arms each having proximal and distal lower occlusion arm ends. The first and second lower occlusion arms define a lower main body width dimension. A lower arcuate portion connects the first and second lower occlusion arms at their distal ends. The occlusion clip further comprises a torsion spring connecting the proximal end of the first lower occlusion arm to the proximal end of the second upper occlusion arm. The torsion spring biases the upper and lower occlusion members toward a closed position wherein the upper occlusion member is in contact with the lower occlusion member.

27 Claims, 14 Drawing Sheets

U.S. PATENT DOCUMENTS

| | | | |
|---|---|---|---|
| 5,474,567 A | 12/1995 | Stefanchik et al. | |
| 5,501,693 A | 3/1996 | Gravener | |
| 5,575,802 A | 11/1996 | McQuilkin et al. | |
| 5,593,414 A | 1/1997 | Shipp et al. | |
| 5,601,573 A | 2/1997 | Fogelberg et al. | |
| 5,601,574 A | 2/1997 | Stefanchik et al. | |
| 5,634,932 A | 6/1997 | Schmidt | |
| 5,681,330 A | 10/1997 | Hughett et al. | |
| 5,833,700 A | 11/1998 | Fogelberg et al. | |
| 5,858,018 A | 1/1999 | Shipp et al. | |
| 5,921,997 A | 7/1999 | Fogelberg et al. | |
| 5,993,465 A | 11/1999 | Shipp et al. | |
| RE36,720 E | 5/2000 | Green et al. | |
| 6,139,555 A | 10/2000 | Hart et al. | |
| 6,193,732 B1 | 2/2001 | Frantzen et al. | |
| 6,241,740 B1 | 6/2001 | Davis et al. | |
| 6,290,575 B1 | 9/2001 | Shipp | |
| 6,350,269 B1 * | 2/2002 | Shipp et al. | 606/143 |
| 6,352,541 B1 | 3/2002 | Kienzle et al. | |
| 6,464,710 B1 | 10/2002 | Foster | |
| 6,527,786 B1 | 3/2003 | Davis et al. | |
| 6,537,289 B1 | 3/2003 | Kayan et al. | |
| 6,599,298 B1 | 7/2003 | Forster et al. | |
| 6,607,540 B1 | 8/2003 | Shipp | |
| 6,652,539 B2 | 11/2003 | Shipp et al. | |
| 6,652,545 B2 | 11/2003 | Shipp et al. | |
| 6,679,894 B2 | 1/2004 | Damarati | |
| 6,824,547 B2 | 11/2004 | Wilson, Jr. et al. | |
| 6,849,079 B1 | 2/2005 | Blake, III et al. | |
| 6,869,435 B2 | 3/2005 | Blake, III | |
| 6,880,699 B2 | 4/2005 | Gallagher | |
| 6,911,033 B2 | 6/2005 | de Guillebon et al. | |
| 6,945,979 B2 | 9/2005 | Kortenbach et al. | |
| 2004/0097972 A1 | 5/2004 | Shipp et al. | |
| 2004/0106396 A1 | 6/2004 | Segura et al. | |
| 2004/0106936 A1 | 6/2004 | Shipp et al. | |
| 2005/0119677 A1 | 6/2005 | Shipp | |
| 2005/0149063 A1 | 7/2005 | Young et al. | |
| 2006/0129168 A1 * | 6/2006 | Shipp | 606/151 |

FOREIGN PATENT DOCUMENTS

| | | |
|---|---|---|
| WO | WO-99/52413 | 10/1999 |

OTHER PUBLICATIONS

Supplemental Search Report for EP2004757136.9.

* cited by examiner

OCCLUSION CLIP AND METHOD OF APPLYING SAME

BACKGROUND OF THE INVENTION

The present invention relates to a medical occlusion clip and more particularly to an occlusion clip suited for sexual sterilization and adapted to be used on a fallopian tube.

Female sterilization, a medical procedure, is accomplished by occluding the fallopian tubes, which stops the egg from being delivered from the ovary to the uterus. Several techniques have been employed for such sterilization which is generally referred to as tubal ligation. One method involves bending the fallopian tube into a knuckle shape and tying a suture about the knuckle to obviate the passage of the egg. Another technique involves cutting the fallopian tube with a mono-polar or bipolar electrocautery and then cauterizing the ends of the tube. Yet another method requires placing a clip over the fallopian tube, the clip serving as a clamp to occlude the fallopian tube and prevent the passage of eggs through the tube.

Tubal ligation may be performed either by an open incision giving access to the fallopian tubes or by laparoscopic intervention which gives access to the fallopian tubes through a small cannula after the female's lower abdominal cavity has been insufflated using a gas such as $CO_2$. The open technique is often used in conjunction with other open procedures such as a Caesarean section for childbirth. In open procedures, ligation can be accomplished effectively using either electrocautery or suture techniques because the working space is adequate to accomplish these procedures. In laparoscopic procedures, however, surgeons are generally limited to either electrocautery or the use of ligation clips.

Ligation clips have generally been of two types. The first type, exemplified by the clips disclosed in U.S. Pat. No. 4,325,377 ('377 Patent) have a latching mechanism that keeps the clip closed once it is clamped around a tube. The clip of the '377 Patent, typically referred to as a "Hulka clip," has two clamping arms with an elastic band at the proximal end of the two arms. The clip is placed around the fallopian tube and then latched about the tube such that the clamping arms occlude the fallopian tube. Another clip of this type, known as a "Filshie clip," is described in U.S. Pat. No. 5,575,802. The Filshie clip is a complex device constructed of two metal arms, a hinge, a latch and a silicon liner covering the two metal arms. The silicone liner gives some degree of resiliency to the clip. The Filshie clip is placed about the fallopian tube and closed by rotating one arm about the hinge point. To latch the clip, one arm is bent by applicator pressure and is engaged by the latch mechanism. The silicon liner compresses the fallopian tube, to a degree dictated by the applicator pressure.

Clips of this type have inherent deficiencies. The Filshie clip, for example, is overly complex, being made of two separate arms, a hinge, a latch and a silicon liner. In addition, the applicator for the Filshie clip must be periodically calibrated to insure proper fallopian tube occlusion pressure.

Both the Filshie and Hulka clips are designed so that the clips must be inserted into the body cavity in a, more or less, open configuration. For laparoscopic procedures this means that the cannula through which the clip is inserted must be large because the clip is in a high profile (i.e., open) state. Typically, the trocar port diameter requirement is from 8 mm to 12 mm depending on the technique used to install the clip. Trocar ports of this size require the procedure to be done in a hospital or similar clinical setting so that general anesthesia is administered to the patient. The added anesthesia cost and facility cost often make the total cost prohibitive. In addition, an 8-12 mm trocar entry wound requires that both the fascia and the skin layers be closed with sutures following the procedure to protect the patient from a postoperative hernia developing.

Another deficiency of the Hulka and Filshie clips is that neither occludes the fallopian tube in more than one place. In addition, the cost of the clips is such that redundancy is not economically practical. This lack of redundancy increases the likelihood of an occlusion failure which can result in an undesired pregnancy. Also, these clips require the use of a reusable single fire applicator.

The second type of clip may be referred to as a "spring clip" and involves the use of a biasing force rather than a latch to maintain a clamping force on the tube. An example of this type of clip is described in U.S. Pat. No. 6,350,269 ('269 Patent). This clip uses a coil spring to bias a clamping arm to clamp a vessel between the clamping arm and a support member. The clip is used in general surgery for occluding vessels and ducts such as the cystic artery and the cystic duct.

The spring clip of the '269 Patent is not suitable for occluding fallopian tubes for a number of reasons. The construction of the bias coils is such that the biasing force decreases as the vas becomes smaller, which often occurs in postpartum fallopian tubes. In addition, the single clamping arm described in the '269 patent is not placed symmetrically with respect to the arms of the support member. As a result, the clip of the '269 Patent does not provide equal occlusion on each side of the clip. Also, the open end of the clamping arm provides a surface that can become snagged on tissue and cause damage.

In general, there are numerous problems associated with the clips that have heretofore been used for tubal ligation. These problems have resulted in a significant failure rate that is attributable to a variety of failure modes. These include failure to maintain an acceptable occlusion force on the tube over time, misapplication by the surgeon, failure of the applicator to apply the proper pressure, and failures due to the complex structure of the clip itself.

Previous clip designs also have limitations with respect to reversibility. Although tubal ligation is generally considered to be a permanent procedure, a growing number of fertility doctors have undertaken procedures for reversing sterilization. As a general matter, the smaller the footprint (i.e., the area affected) of the clip on the fallopian tube, the more likely it will be that a successful reversal of the ligation procedure may be accomplished.

SUMMARY OF THE INVENTION

An aspect of the present invention provides an occlusion clip comprising an upper occlusion member having substantially parallel first and second upper occlusion arms each having proximal and distal upper occlusion arm ends. The first and second upper occlusion arms define an upper main body width dimension. An upper arcuate portion connects the first and second upper occlusion arms at their distal ends. The occlusion clip also comprises a lower occlusion member having substantially parallel first and second lower occlusion arms each having proximal and distal lower occlusion arm ends. The first and second lower occlusion arms define a lower main body width dimension. A lower arcuate portion connects the first and second lower occlusion arms at their distal ends. The occlusion clip further comprises a torsion spring connecting the proximal end of the first lower occlusion arm to the proximal end of the second upper occlusion arm. The torsion spring biases the upper and lower occlusion members toward a closed position wherein the upper occlusion member is in contact with the lower occlusion member.

Another aspect of the invention provides an occlusion clip applicator comprising a jaw push tube, an elongate clip holder, a clip pusher and a pair of jaws. The elongate clip holder is formed as a channel having first and second support rails attached thereto. The first and second support rails are substantially parallel and in alignment with each other. The clip holder has proximal and distal clip holder ends and is disposed inside the jaw push tube interior. The clip pusher has an elongate support member having upper and lower sides with a plurality of clip push fingers attached to the lower side. The support member is mounted within the jaw push tube interior substantially parallel to the clip holder with at least a portion of each clip push finger extending downward into the channel. Each of the jaws has proximal and distal jaw ends, an inner engaging side and an opposite outer side, and a clip slot formed through the jaw from the inner engaging side to the outer side. The clip slot extends distally from and through the proximal jaw end. Each jaw also has a pair of parallel support shelves bounding at least a portion of the clip slot. The jaws are pivotably mounted at their proximal ends to the distal clip holder end and are configured for engagement by the distal tube end for selective rotation between a fully open position and a closed position wherein the engaging sides of the jaws are in contact with each other.

Yet another aspect of the invention provides a method of occluding a fallopian tube of a patient using an occlusion clip. The occlusion clip has an upper occlusion member having substantially parallel first and second upper occlusion arms connected by an upper arcuate portion at their distal ends and a lower occlusion member having substantially parallel first and second lower occlusion arms connected by a lower arcuate portion. A torsion spring connects the proximal end of the first lower occlusion arm to the proximal end of the second upper occlusion arm. The upper and lower occlusion members define a main body width and a maximum arcuate portion width greater than the main body width. The torsion spring provides a pivot axis for rotational separation of the upper occlusion member and the lower occlusion member and a biasing force to bias the occlusion clip toward a closed configuration. The method comprises inserting a first trocar port through an abdominal wall defining an abdominal cavity of the patient, inserting a second trocar port through the abdominal wall of the patent, insufflating the abdominal cavity and inserting an endoscopic camera through the first trocar port to locate and observe the fallopian tube. The method further comprises inserting the occlusion clip through the second trocar port, opening the occlusion clip by rotating the upper occlusion member away from the lower occlusion member, positioning the occlusion clip so that a portion of the fallopian tube is positioned between the upper occlusion member and the lower occlusion member, and releasing the upper and lower occlusion members to engage and occlude the fallopian tube.

DETAILED DESCRIPTION OF THE INVENTION

Figure 1:
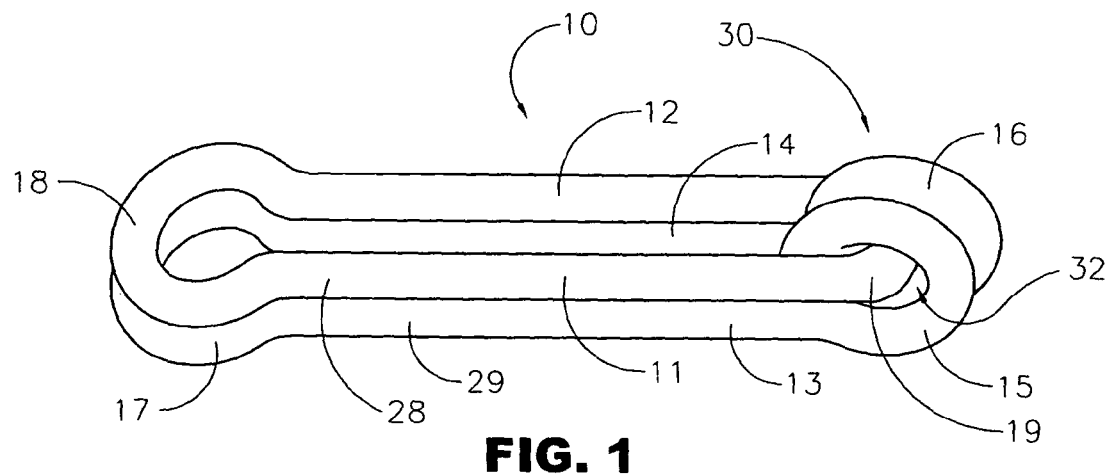
FIG. 1 is a perspective view of an occlusion clip according to an embodiment of the invention.

Embodiments of the present invention include a spring occlusion clip that can be installed over a fallopian tube or similar vas using a laparoscopic procedure through a 3 mm trocar port. The occlusion clip may be inserted though a trocar cannula in a partially open position and then further opened inside the body cavity. This allows the use of a smaller cannula than the previous clips that must be inserted in a high profile open state.

The occlusion clip of the present invention comprises two parallel occluding members each consisting of two parallel arms. The two pairs of adjacent arms occlude the fallopian tube at two points that may be less than 2.0 mm apart, thus providing a double occlusion and imparting a kinking of the fallopian tube for safer, more reliable occlusion. The occlusion clips of the invention may have torsion coils that bias the occluding members toward the closed position and connect the arms of the clip. Once the clips are applied, a biasing force applies a clamping pressure to the fallopian tube. The clips may be configured so that the biasing force is maintained or increased if and when the diameter of the tube decreases. The biasing force may be maintained even in the event of the tube separating into two pieces.

With reference to FIGS. 1-7 an occlusion clip 10 according to an embodiment of the invention will now be discussed in more detail. The occlusion clip 10 has a top occlusion member 28 formed in a first plane and a bottom occlusion member 29 formed in a second plane that is substantially parallel to the first plane. The top occlusion member 28 has a top left arm 11 and a substantially parallel top right arm 12 that are spaced apart by a predetermined spacing distance $W_s$. The bottom occlusion member 29 has a bottom left arm 13 and a substantially parallel bottom right arm 14 that are preferably spaced apart by the same distance as the top left arm 11 and top right arm 12. The arms 11, 12, 13, 14 serve to define an overall main body width $W_b$.

The top occlusion member 28 has a first free end member 21 connected to the top left arm 11. The first free end member 21 angles downward slightly and has an approximately 90 degree bend 19 that allows end of the free end member 21 to be tucked inside the torsion spring 30. The distal ends of the top left arm 11 and the top right arm 12 are connected to a first arcuate section 18 that is coplanar with the top left arm 11 and the top right arm 12. The bottom occlusion member 29 has a second free end member 22 connected to the bottom right arm 14. The second free end member 22 angles upward slightly and has an approximately 90 degree bend 20 that allows the end of the second free end member 22 to be tucked inside the torsion spring 30 on the opposite side of the spring 30 from the first free end member. The distal ends of the bottom left arm 13 and the bottom right arm 14 are connected to a second arcuate section 17 that is coplanar with the bottom left arm 13 and the bottom right arm 14.

The top and bottom occlusion members 28, 29 are connected by a torsion spring 30 having a plurality of torsion coils. Although the illustrated embodiment shows the spring 30 having two coils, it will be understood that any number of coils may be used. The proximal end of the top right arm 12 of the top occlusion member 28 is connected to a first torsion coil 16, which is connected to a second torsion coil 15 that lies in a plane approximately parallel to the first torsion coil 16. The second torsion coil 15 is further connected to the bottom left arm 13 of the bottom occlusion member 29. The torsion coils collectively define a central passage 32 through the middle of the spring 30.

The occlusion clip 10 is preferably formed from a single wire segment that is bent and shaped to form the features described above. When so-formed, the first free end member 21 is formed by one end portion of the wire segment and the second free end member 22 is formed by an end portion at the opposite end of the wire segment. The occlusion clip 10 may be formed so that the first and second free end members 21, 22 are at least partially disposed within the central passage 32 of the spring 30. This assures that the ends of the wire from which the occlusion clip 10 is formed are not exposed, thereby reducing or eliminating the likelihood of snagging.

Figure 2:
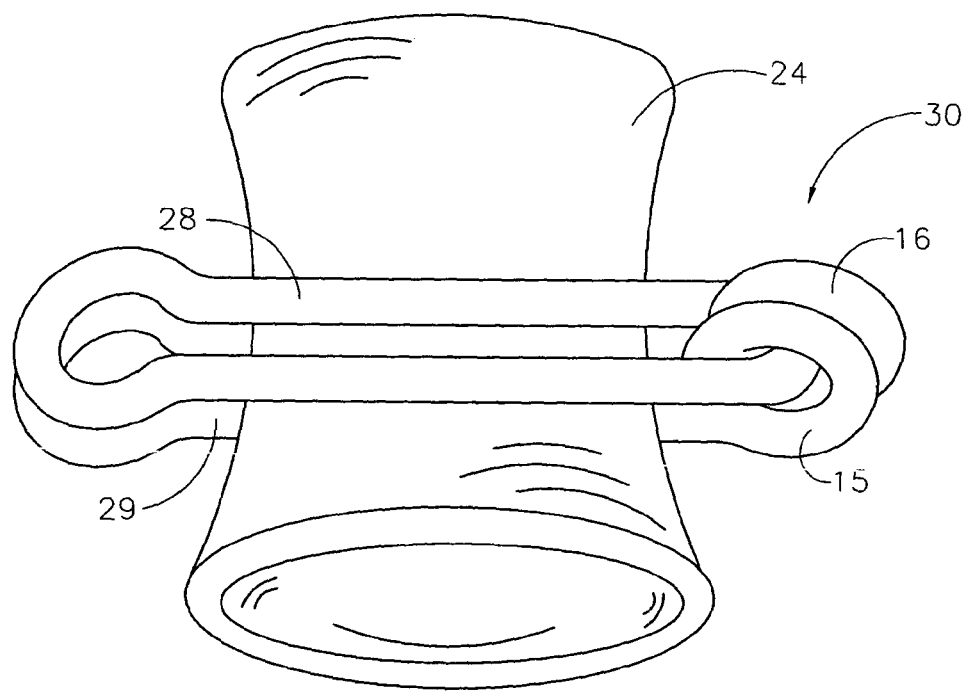
FIG. 2 is a perspective view of the occlusion clip of FIG. 1 applied to a fallopian tube.
Figure 3:
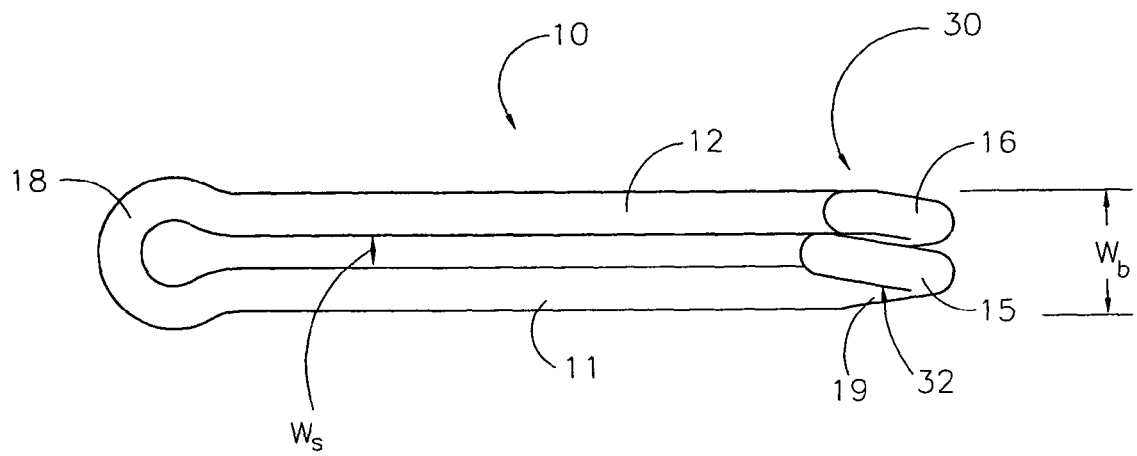
FIG. 3 is a plan view of the occlusion clip of FIG. 1.
Figure 4:
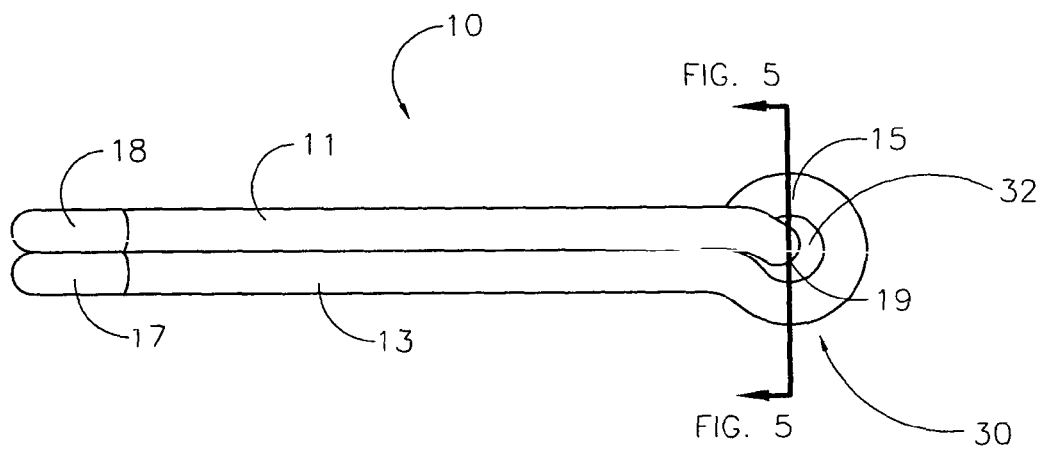
FIG. 4 is a side view of the occlusion clip of FIG. 1.
Figure 5:
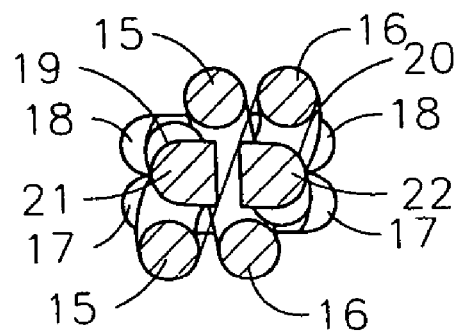
FIG. 5 is a section view of the occlusion clip of FIG. 1.
Figure 6:
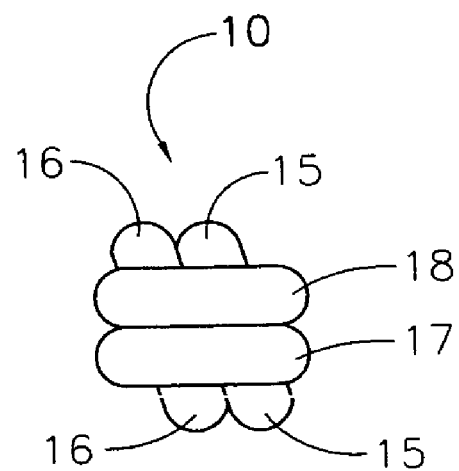
FIG. 6 is an end view of the of the occlusion clip of FIG. 1.

As illustrated in FIGS. 1 and 3-6, the occlusion clip 10 is in a closed position wherein the top occlusion member 28 is in contact with the bottom occlusion member 29. The torsion coils 15, 16 of the torsion spring 30 serve to bias the occlusion members 28, 29 to adopt this closed position. The occlusion clip 10 may be opened by separating the top and bottom occlusion members 28, 29 so that they pivot approximately about an axis perpendicular to and centered within the first and second torsion coils 15, 16. Once opened, the occlusion clip 10 may be positioned over a fallopian tube with the bottom occlusion member 29 underneath the vas and the top occlusion member 28 above the vas. When the occlusion members 28, 29 are released, the biasing force of the torsion spring 30 causes the occlusion members 28, 29 to move toward the closed position, thereby clamping to and occluding the fallopian tube 24 as shown in FIG. 2.

The clip 10 is configured so that as the clip 10 is opened and the top and bottom occlusion members 28, 29 are separated, the diameter of the torsion coils 15, 16 is increased, which has the effect of decreasing the biasing force of the torsion spring 30. Thus, the effect of opening the clip 10 is to reduce the reaction force that may be exerted by the occlusion members 28, 29. Conversely, if the occlusion members 28, 29 are released so as to return toward the closed position, the biasing force exerted by the spring 30 increases as the separation of the occlusion members 28, 29 decreases. Thus, the reaction force exerted by the occlusion members 28, 29 on the fallopian tube increases as the fallopian tube is constricted and the occlusion members 28, 29 approach the closed position. Moreover, if and when the fallopian tube 24 becomes smaller because of a reduction in swelling or necrosis, the pressure exerted by the clip 10 on the fallopian tube 24 increases, thereby safely keeping eggs from traversing the occluded site.

It will be understood that the actual level of the biasing force and the relationship between occlusion member separation distance and the biasing force are dependent on the properties of the wire (e.g., material and gauge), the number of torsion coils and the closed diameter of the torsion coils.

As shown in FIGS. 1-7, the arcuate sections 17, 18 may be sized to extend outside the main body width of the occlusion clip 10 in order to facilitate manipulation and application of the clip 10. This extension is particularly useful in facilitating clip application using the clip appliers are discussed hereafter.

Figure 7:
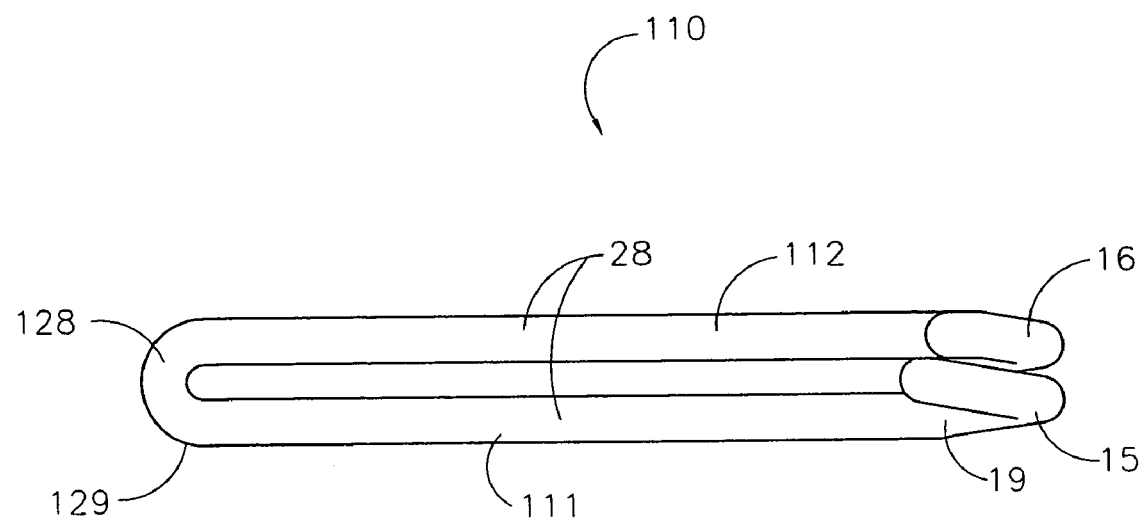
FIG. 7 is a plan view of an occlusion clip according to an embodiment of the invention.
Figure 8:
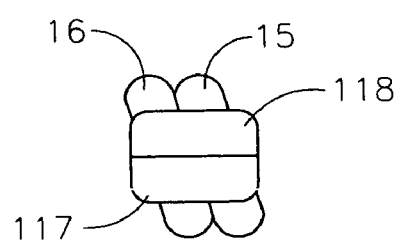
FIG. 8 is a side view of the occlusion clip of FIG. 7.

In an alternative embodiment shown in FIGS. 7 and 8, however, an occlusion clip 110 has arcuate sections 117 and 118 that are sized so that the left arms 111 and the right arms 112 intersect the arcuate sections 117, 118 as tangents to the arcuate sections 117, 118. This results in substantially U-shaped occluding members 128, 129. The operation and performance of the occlusion clip 110 of FIGS. 7 and 8 are substantially similar to those of the occlusion clip 10 of FIGS. 1-6.

The occlusion clips of the invention may be made from any thin wire stock that is suitable for surgical use and that has sufficient strength, resilience and durability. One exemplary material is titanium wire, which has proven suitable in thicknesses ranging from about 10 mils to about 40 mils and particularly suitable in thicknesses ranging from about 15 mils to about 30 mils. Stainless steel wire may also be used.

Using 10-40 mil wire, the torsion coils 15 and 16 may be formed with a diameter less than 0.100 in. The main body width of the occlusion clip may also be less than 0.100 in. An effective overall length (proximal end to distal end) of the occlusion clip may be in a range from 0.25 in. to 1.00 in. A particularly efficacious length may be in a range from about 0.40 in. to about 0.60.

An exemplary occlusion clip according to the invention formed from 25 mil wire with a 0.10 in. coil diameter, a main body width of 0.10 in. and an over all length of about 0.50 in. provides a clamping load of about 0.48 pounds when the occlusion members are opened to form a 20-24 degree clip opening angle. This force is more than adequate for occluding a fallopian tube.

As will be discussed in more detail hereafter, one or more occlusion clips 10 may be loaded into a clip applicator and inserted into the surgical field, either directly, in the case of open surgery, or through a trocar cannula. The small size of the clips 10 and the ability to introduce the clips in a closed or nearly closed configuration make possible the use of a cannula as small as 3 mm in diameter. The applicator is preferably configured so that when triggered, the applicator causes the distal most clip 10 of a series of clips 10 to be moved distally over controlling surfaces in contact with one or both of the occlusion members 28, 29. The applicator is also preferably configured to open the distal-most clip 10 and insert it over the fallopian tube 24 to be occluded. The clip 10 would then be released form the applicator and allowed to close, thus occluding the fallopian tube. The applicator would then be ready to insert another clip 10 over this or another vas after resetting. When the occlusions are complete, the applicator is removed from the surgical field.

Advantageously, the occlusion clips of the present invention may be formed in a symmetric manner so that they may be inverted without any change in their application or functionality.

A single occlusion clip of the invention may be used to occlude the fallopian tube at two points that are less than 2 mm apart. This double clamping of the fallopian tube allows for a degree of kinking of the fallopian tube between the clamping points which contributes to a more reliable occlusion. The configuration of the torsion coils of the clips according to the invention has the dual advantage of eliminating the need for a latch or hinge while assuring that the clamping force of the clip does not decrease as the fallopian tube shrinks after application. Finally, because the clip affects only a very small area of the fallopian tube (less than 2.5 mm along its length) the reversibility of the sterilization process is enhanced.

Figure 9:
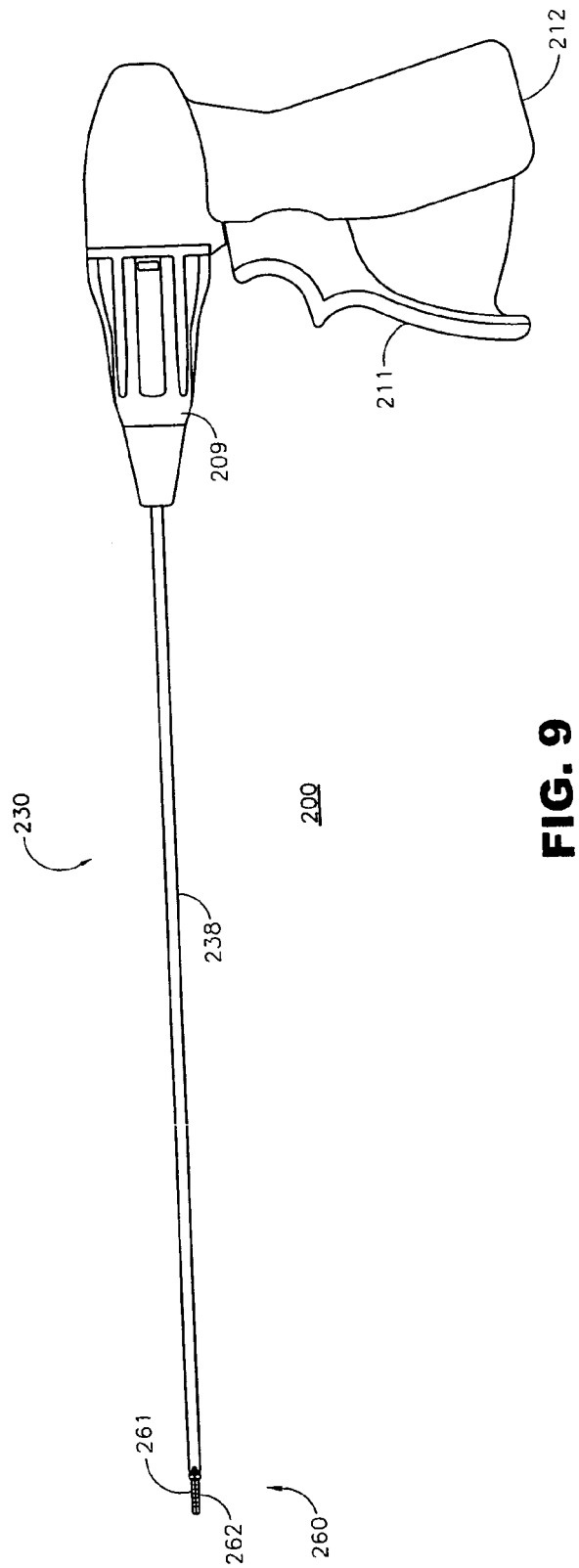
FIG. 9 is a side view of a clip applicator according to an embodiment of the invention.

The occlusion clips of the invention are adaptable so that a plurality of clips may be loaded into a clip holder or magazine for ejection and application by an applicator configured for easy manipulation and one handed use by a surgeon. The clips may be sized to fit through a 3 mm trocar port. Turning now to FIGS. 9-20, an occlusion clip applicator 200 according to an embodiment of the invention will be described. As shown in FIG. 9, the applicator 200 comprises a handle/actuation assembly 210, a tube assembly 230 and a jaw assembly 260 sized to be inserted through a 3 mm trocar port. As will be discussed in more detail, the tube assembly 230 includes a clip holder 233 configured to hold a plurality of occlusion clips 10 of the type previously described. The length of the tube assembly 230 can vary depending on its intended use. For laparoscopic procedures, a length of 12 to 15 inches may be desirable. For non-laparoscopic use a 4 to 8 inch length may be sufficient. A pair of jaws 261, 262 attached to the distal end of the clip holder 233 are configured to be positioned around and selectively engage a fallopian tube or other vas. To assist in this engagement, the tube assembly 230 and jaw assembly 260 may be rotated through 360 degrees relative to the handle/actuation assembly 210. When a trigger 211 in the handle/actuation assembly 210 is pulled, the jaws 261, 262 close over the fallopian tube and an occlusion clip 10 is pushed distally out of the clip holder 233 and over a ramp onto a central groove in the engaged jaws, 261, 262. The ramp forces the occlusion members 28, 29 apart a sufficient amount so that the clip 10 may be placed around the fallopian tube. The jaws 262, 262 are configured so that when the clip 10 is pushed distally far enough, the clip 10 automatically disengages from the jaws 262, 262, whereupon the occlusion members 28, 29 close to engage and occlude the fallopian tube.

Figure 10:
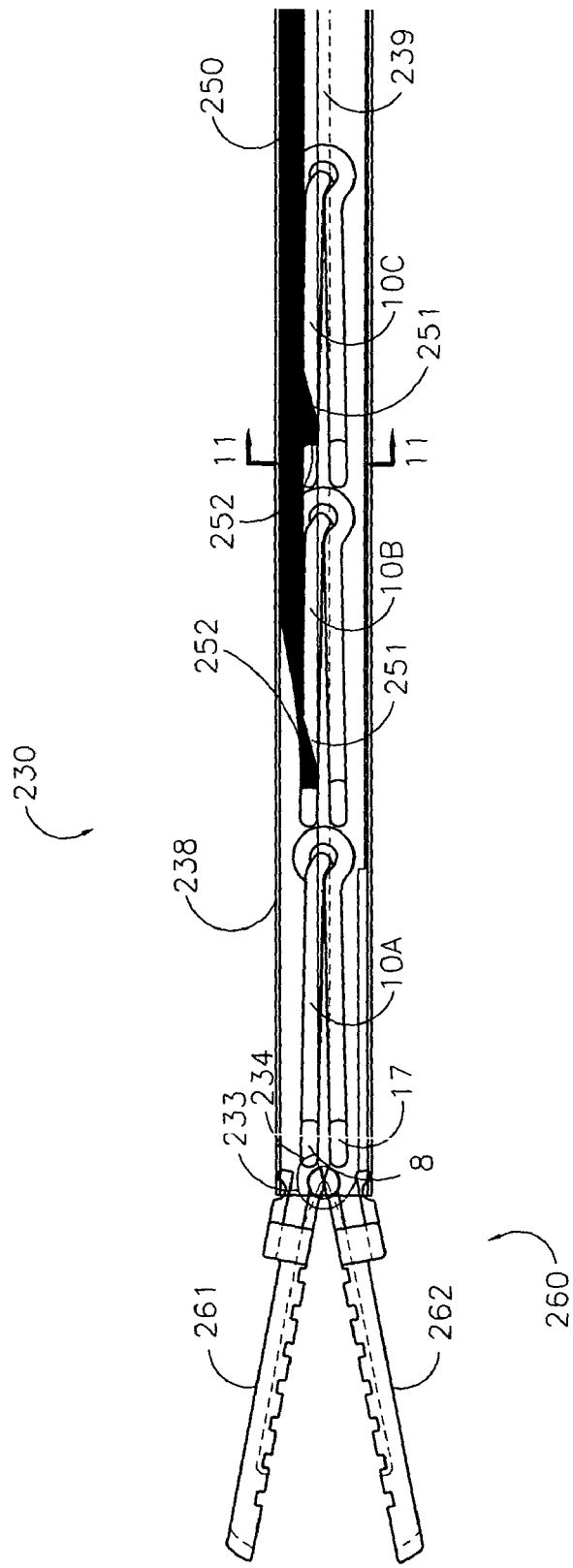
FIG. 10 is a section view of a portion of the clip applicator of FIG. 9 in an initial or reset configuration.
Figure 11:
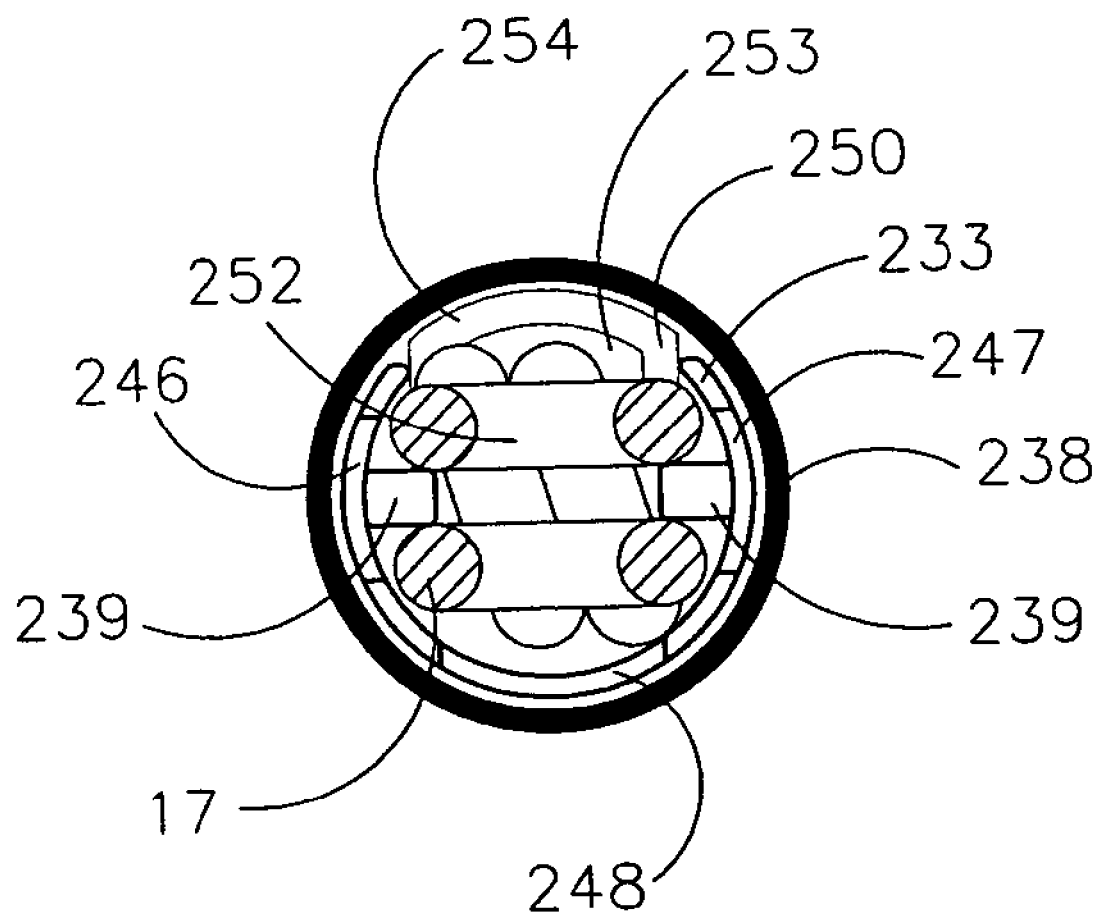
FIG. 11 is a section view of a portion of the clip applicator of FIG. 9 in an initial or reset configuration.
Figure 12:
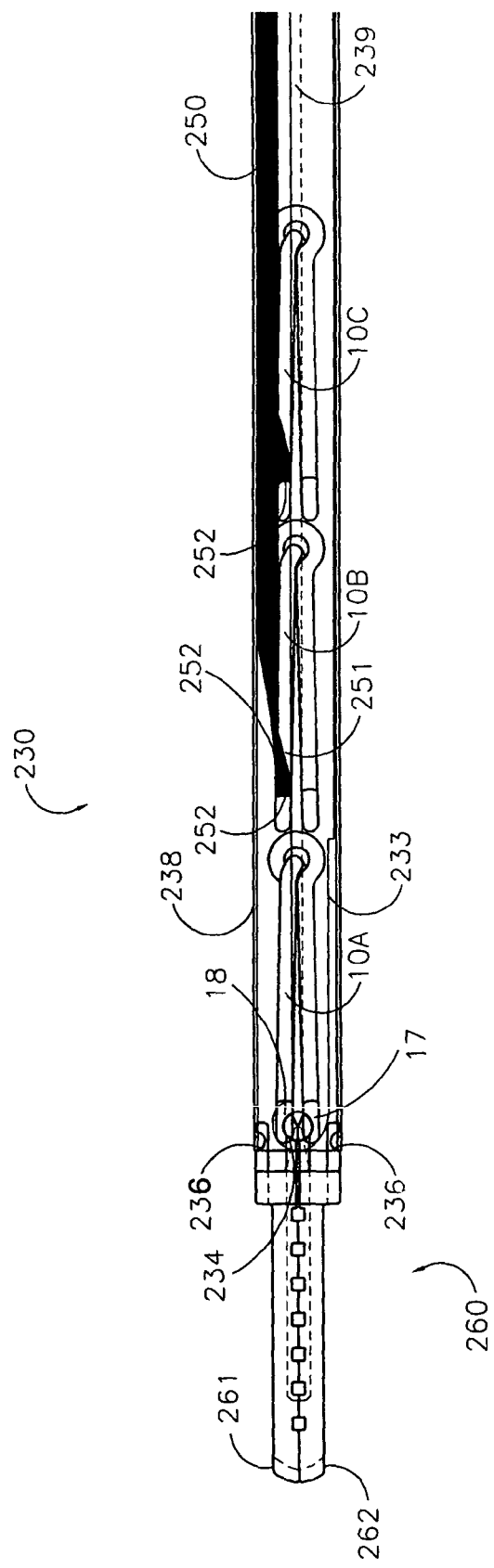
FIG. 12 is a section view of a portion of the clip applicator of FIG. 9 during a clip ejection event.
Figure 13:
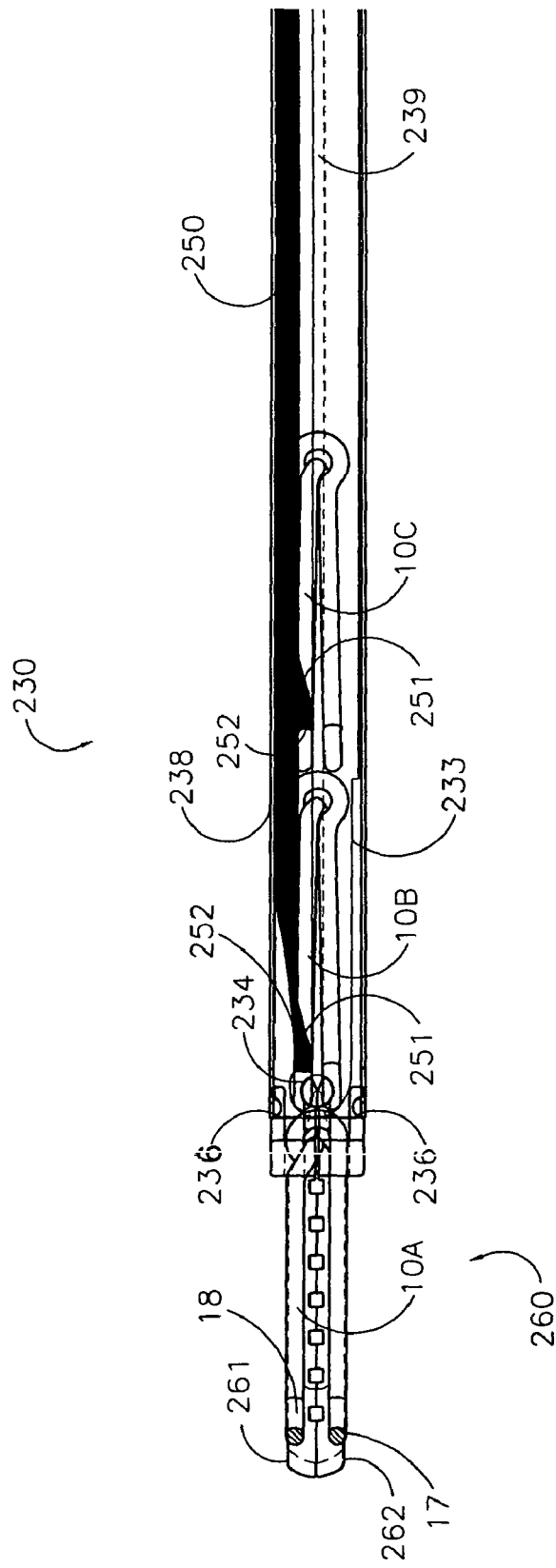
FIG. 13 is a section view of a portion of the clip applicator of FIG. 9 during a clip ejection event.

FIGS. 10-14 illustrate a jaw assembly 260 of the clip applicator 200 according to an embodiment of the invention. FIGS. 10, 12 and 13 show the jaw assembly 260 and the distal portion of the tube assembly 230 at three stages of operation illustrating: (1) the initial or reset stage of the applicator 200 where the jaw assembly 260 is in a fully open configuration; (2) an intermediate stage wherein the jaw assembly is in a closed or engagement position and a clip 10 is just entering the jaw assembly 260; and (3) a stage wherein the jaw assembly 260 remains in the closed or engagement position and a clip 10 is in its final position in the jaw assembly 260 just prior to release of the clip 10 from the applicator 200. Although not shown in FIGS. 12 and 13, it will be understood that a fallopian tube or other vas would be positioned between the jaws 261, 262 when the jaw assembly 260 in the closed or engagement position.

As best seen in FIGS. 10 and 11, the tube assembly 230 comprises a jaw push tube 238 in which the clip holder 233 is disposed. The jaw push tube 238 and the clip holder 233 are independently attached to the handle/actuation assembly 210 so that the jaw push tube 238 can be moved distally and proximally along its longitudinal axis while the clip holder 233 remains stationary. The clip holder 233 has two opposing side members 246, 247 connected by a base member 248, which combine to form a channel with a curved, U-shaped cross section. In an alternative embodiment, the side members 246, 247 are substantially straight rather than curved. In this embodiment, a pair of spacers may be disposed between the side members 246, 247 and the inner surface of the jaw push tube 238 to hold the clip holder 233 in position within the jaw push tube 238.

The clip holder 233 has two opposing support rails 239 attached to the inner surfaces of the side walls 246, 247 for supporting and positioning a plurality of occlusion clips 10. Occlusion clips 10 are loaded into the clip holder so that the outer edges of the arcuate portions 17, 18 of the clips 10 engage the support rails 239 with the first (or upper) arcuate portion 17 engaging the top of the rails 239 and the second (or lower) arcuate portion 18 engaging the bottom of the rails 239. This has the effect of keeping the occlusion members 28, 29 of the clips 10 in a slightly open configuration. The rails 239 are sized and spaced so that the clips 10 may slide along the rails without interference from the occlusion members 28, 29 and the spring 30. The clips 10 are loaded with the arcuate portions 17, 18 pointed toward the distal end of the clip holder 233. Although any number of clips 10 may be loaded within the clip holder 233 an example configuration with three clips 10A, 10B, 10C is shown in FIGS. 10 and 12. With the exception of the distal-most clip 10A, each clip 10 in the clip holder 233 is positioned so that the distal tip of its arcuate portions 17, 18 engage the tension coils 15, 16 of the clip 10 just distal to it. Thus, in the illustrated example, the distal end of the second clip 10B engages the proximal end of the first clip 10A. As a result, a distal movement of clip 10B along the rails 239 will cause a corresponding distal movement of clip 10A.

Also disposed within the jaw push tube 238 is a clip pusher 250. The clip pusher 250 has an elongate support member 254 to which is attached at regular intervals a plurality of parallel clip push fingers 251. The support member 254 and the clip push fingers 251 combine to form a channel 253. The clip push fingers 251 angle downward from the support member 254. Each clip push finger 251 terminates in a clip engagement foot 252, which is shaped to engage the proximal sides of the upper arcuate portion 17 of the occlusion clips 10.

The clip pusher 250 is configured so that distal movement of the support member 254 causes distal movement of all of the clips 10 in the clip holder 233. The clip pusher 250 may be configured to engage all but the distal-most clip 10A. Accordingly, in this embodiment, the number of clip push fingers 254 is equal to or greater than the number of clips 10 loaded in the clip holder 233.

As will be discussed, the clip pusher 250 may be used in conjunction with the actuator 290 of the handle/actuation assembly 210 to selectively cause the loaded clips 10 to slide distally along the rails 239 toward the jaw assembly 260.

The jaw assembly 260 comprises an upper jaw 261 and a lower jaw 262 that are pivotably mounted to the distal end of the clip holder 233 at a jaw pivot axis 234. FIGS. 14-19 illustrate the features of the upper jaw 261. It will be understood that the features of the lower jaw 262 are identical to those of the upper jaw 261 and that the descriptions that follow apply equally to both. The jaw 261 has an engagement portion 270 attached to a pivot portion 280. The engagement portion 270 comprises first and second jaw side members 271, 272 connected by a proximal end member 273, the three of which combine to define a U-shaped plan-form with a central slot 265 terminating in an ejection opening 266. The engagement portion 270 has an inner engaging surface 256 on one side (lower side of the upper jaw 261 and upper side of the lower jaw 262) and an outer surface 257 on the opposite side from the inner engaging surface 256. The jaws 261, 262 are mounted so that their inner engaging surfaces face toward one another. The central slot 265 forms a passage completely through the inner engaging surface 256 and the outer surface 257.

The jaw side members 271, 272 each have a clip support shelf 269 adjacent the central slot 265. The central slot 265 and the clip support shelf 269 are sized and configured so that when the jaws 261, 262 are in the closed or engaging position shown in FIGS. 12 and 14, an occlusion clip 10 may slide along the central slot 265 with the outer edges of the arcuate portion 17 of the clip 10 engaging and being supported by the clip support shelves 269 of the upper jaw 261 and the arcuate portion 18 of the clip 10 engaging and being supported by the clip support shelves of the lower jaw 262. In this engaging position, the clip slots 265 of the upper and lower jaws 261, 262 are aligned so that the main body and the spring 20 of the clip 10 can be passed distally along the slots 265. The support shelves 269 of the upper jaw 261 and the support shelves of the lower jaw 262 are spaced apart so that a clip 10 positioned within the clip slot 265 is opened a sufficient amount that the upper occlusion member 17 can be positioned above the vas to be occluded and the lower occlusion member 18 can be positioned below the vas to be occluded. This fully opened clip configuration is obtained by sliding the clip 10 over a pair of clip entrance ramps 267 that bound the clip slot 265 at the proximal end of the jaw 261. The proximal ends of the ramps 267 match and are aligned with the clip support rails 239 of the clip holder 233. The distal ends of the ramps 267 blend into the support shelves 269.

At its distal end, the clip slot 265 terminates in a clip ejection opening 266. The clip ejection opening 266 may be any shape sufficient to allow the passage of the arcuate portions 17, 18 of the clip 10 to pass therethrough. The clip ejection opening 266 thus will have a diameter or effective width that is greater than the maximum width dimension of the arcuate portions 17, 18 of the clip 10. It will be understood that when a clip 10 is pushed distally along the clip slot 265, the outer edges of the arcuate portion 17 of the clip 10 is supported by the support shelves until the arcuate portion 17 reaches the ejection opening 266. At this point, the biasing force of the clip causes the arcuate portion 17 to drop through the ejection opening 266. Simultaneously, the arcuate portion 18 of the lower occluding member 29 passes through the corresponding ejection opening of the lower jaw 262 and the clip 10 is released from the applicator 200.

The upper and lower jaw engagement members 270 are configured to engage a fallopian tube or other vas on both sides of a location to be occluded. As will be discussed, the upper and lower jaws 261, 262 may be selectively rotated from a reset position as in FIG. 10 to an engagement position as in FIGS. 11 and 12. The applicator 200 may be configured so that the jaws 261, 262 provide only a sufficient clamping force to hold the jaw assembly 260 in place long enough to place and eject an occlusion clip 10. The lower surface of the jaw engagement side members 271, 272 may include a plurality of serrations or teeth 268, which assist in positioning the fallopian tube or vas within the jaws 261, 262.

The pivot portion of the jaw 261 has a left axle 264 and a right axle 263, which are each formed as partial cylinders. These axles are configured for insertion into corresponding bearing holes in the distal end of the clip holder 233. The pivot portion 280 also has a base structure 274 to which is attached to a tube engagement member 275. The tube engagement member 275 includes an engagement groove 236 and is configured for engagement by the distal end of the jaw push tube 238. When the jaw 261 is attached to the clip holder 233 at the pivot axis 234, a distal movement of the jaw push tube 238 relative to the clip holder 233 causes the distal end of the jaw push tube 238 to engage the tube engagement member 275 at the engagement groove 236 and move it in a distal direction. This causes the upper jaw 261 (and the lower jaw 262) to rotate from the initial or reset position of FIG. 10 toward the vas engagement position of FIGS. 12 and 14. The jaws 261, 262 are biased to the reset position so that subsequent proximal movement of the push tube 238 allows the jaws 261, 262 to return to the reset position.

Figure 20:
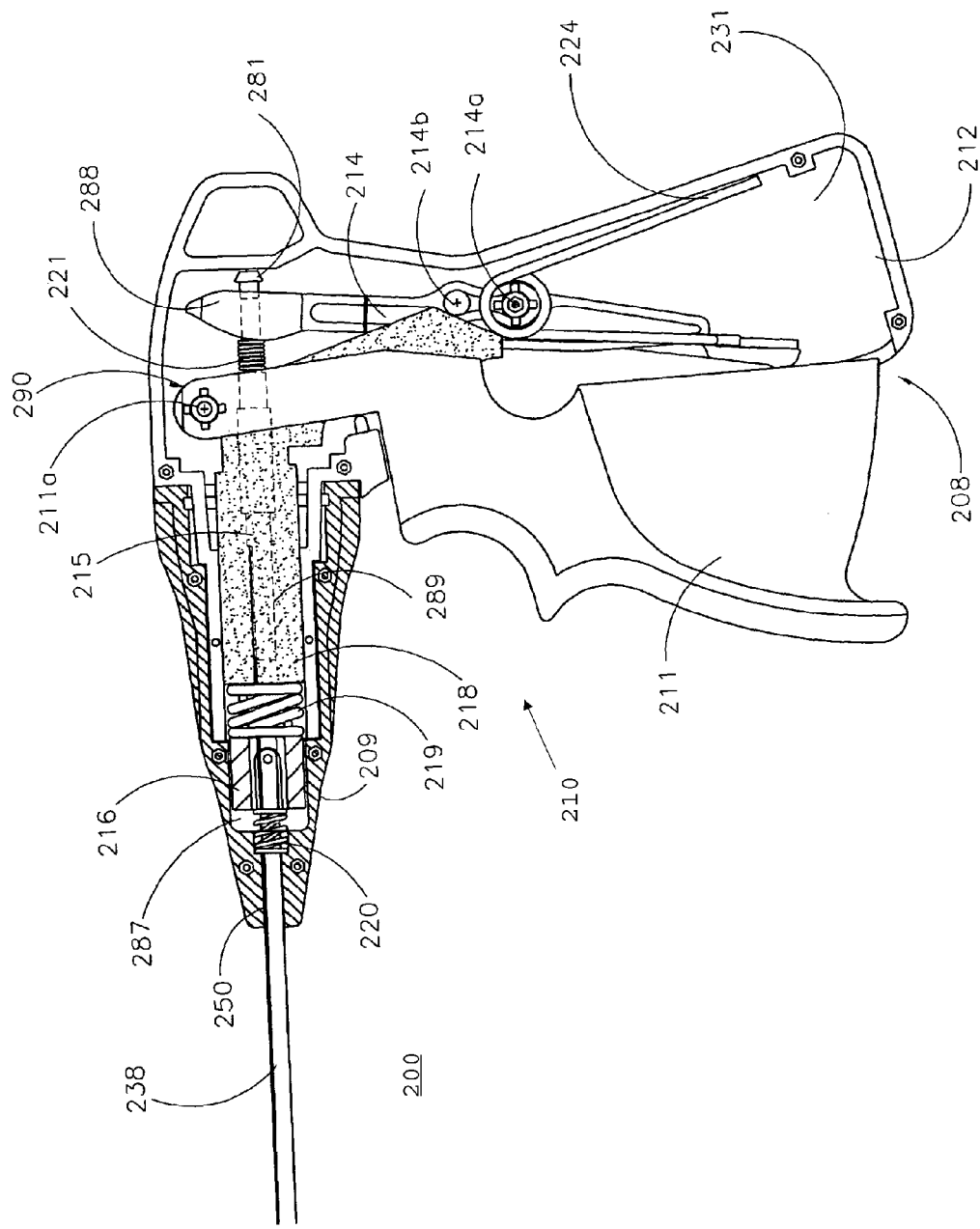
FIG. 20 is a section view of a handle/actuation assembly of a clip applicator according to an embodiment of the invention.

FIG. 20 is a section view of a handle/actuation assembly 210 that may be used in the applicator 200. The handle/actuation assembly 210 has a handgrip portion 208, a tube housing 209 and an actuator 290. The handgrip portion 208 comprises a handgrip 212 to which a trigger 211 is pivotably attached by trigger pivot 211a. It will be understood that only one side of the handgrip 212 is shown in FIG. 9 and that the complete handgrip 212 defines a handgrip interior space 231. The handgrip 231 has an opening on its distal side that is sized to allow a portion of the trigger 211 to pass into the handgrip interior space 231 when the trigger 211 is rotated proximally (counterclockwise, as shown in FIG. 22). The trigger 211 and the handgrip 212 may be configured so that a portion of the trigger 211 is always disposed within the handgrip interior space 231.

The tube housing 209 is rotatably attached to the handgrip 212 and defines a tube chamber 287. The actuator 290 is disposed within the tube chamber 287 and the handgrip interior space 231. The actuator 290 is configured to sequentially operate the jaw assembly 260 and the clip pusher 250 so as to allow the selective placement and ejection of occlusion clips by the user. It will be understood that the actuator mechanism illustrated is one of a variety of mechanisms that could be used in the applicator 200 of the invention. The tube housing 209 may be formed with a generally conical shape contoured to facilitate gripping and rotating the tube housing 209.

In the illustrated embodiment, the actuator 290 comprises a main actuator link member 214 that is pivotably attached to the handgrip 212 by pivot 214a. The main actuator link member 214 is configured for engagement by the trigger 211 to cause the main actuator link member to rotate about the pivot 214a. The main actuator link member 214 has a boss 214b to which is attached a reset spring 224. The reset spring 224 engages the trigger 211 to bias the trigger 211 to the reset position shown in FIG. 9. The main actuator link 214 has an opening adjacent its upper end 288 through which the proximal end of an actuator rod 281 is disposed.

The actuator 290 further comprises a sub-actuator 215 that has an annular portion through which the actuator rod 281 passes. The sub-actuator 215 is attached to the proximal end of the clip pusher 250 and is slidably disposed within a cylindrical inner sleeve 289. The cylindrical inner sleeve 289 is disposed within a passage in a cylindrical jaw pusher 218 that engages a first jaw spring 219 at its distal end. A cylindrical jaw actuator 216 is disposed between the first jaw spring 219 and a second jaw spring 220. The jaw actuator 216 is slidably disposed in a cylindrical passage within the tube housing 209.

When the trigger 211 is rotated proximally the main actuator link 214 is rotated about pivot axis 214a. As a result, the main actuator link 214 applies a distal force on sub actuator 215 via actuator spring 221. Simultaneously, the main actuator link 214 moves jaw pusher 218 distally via contact at boss 214b (actual contact point not shown) against first jaw spring 219. The first jaw spring 219 applies a distal force on the jaw actuator 216, which causes the jaw push tube 238 to move distally so that the distal end of the jaw push tube 238 engages the jaw engagement grooves 236, thereby causing jaws 261 and 262 to rotate toward the engagement position.

As the trigger 211 is rotated further around the pivot 211A, the force applied to the sub-actuator 215 by the main actuator link 214 is increased. This force is transmitted by the sub-actuator 215 to the clip pusher 250, which, in turn, transmits the force through the clip push fingers 251 to the proximal pusher 253 and the clips 10 in the clip holder 233. When the applied force exceeds the friction between the clips 10 and the support rails 239, the clips 10 begin to move distally. The proximal pusher 253 and the clips 10 all advance in force contact with each other.

FIGS. 12 and 13 illustrate an intermediate stage in the process of ejecting a clip 10 from the applicator 200. At this stage, the jaws 261, 262 have been rotated to their engagement position and the distal most clip 10a has been pushed distally so that the arcuate portions 17, 18 of clip 10a have engaged and started up the entrance ramps 267. This causes the further separation of the occluding members 28, 29.

Figure 14:
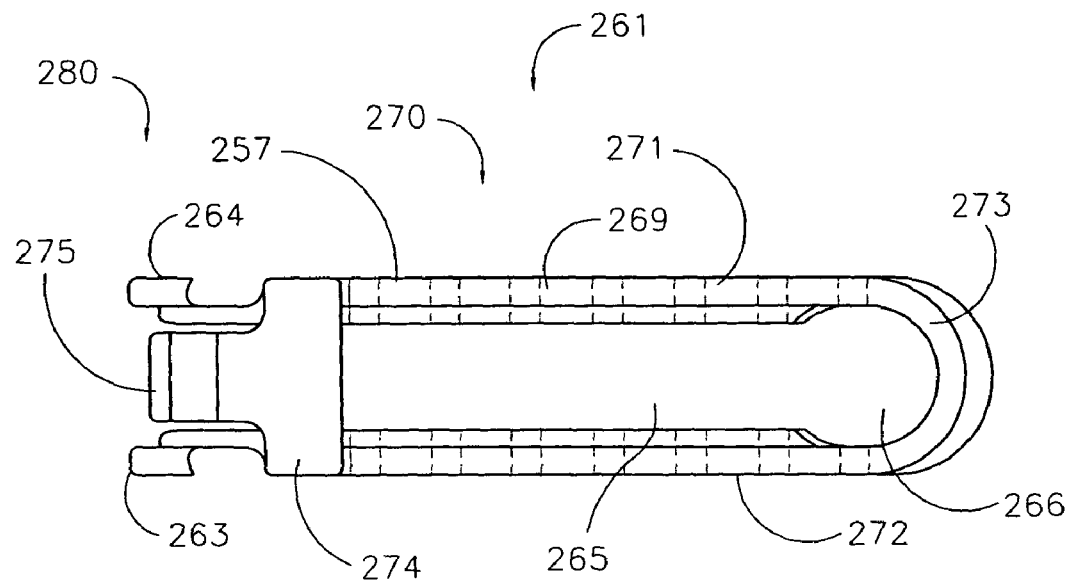
FIG. 14 is a top plan view of vas engagement jaw of a clip applicator according to an embodiment of the invention.
Figure 15:
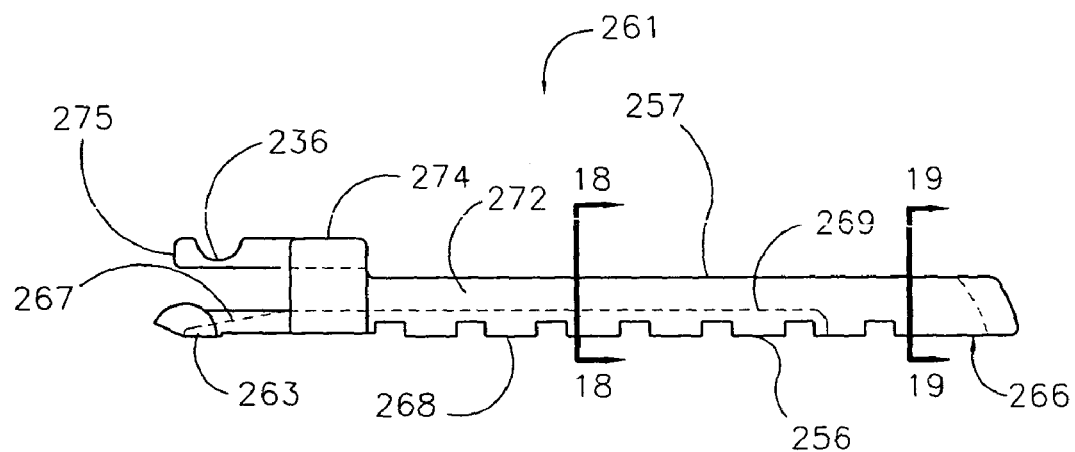
FIG. 15 is a side view of the vas engagement jaw of FIG. 15.
Figure 16:
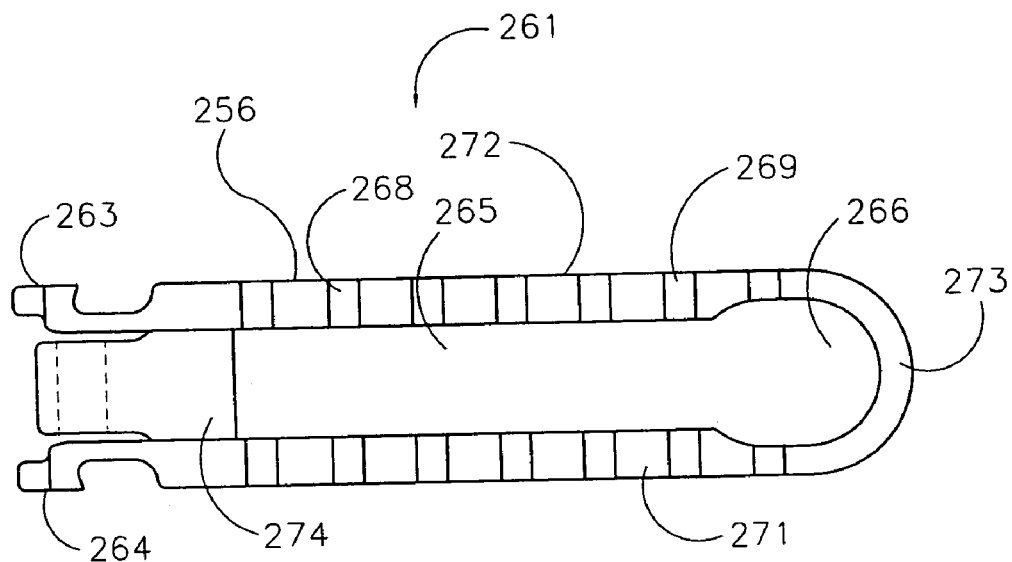
FIG. 16 is a bottom plan view of the vas engagement jaw of FIG. 15.
Figure 17:
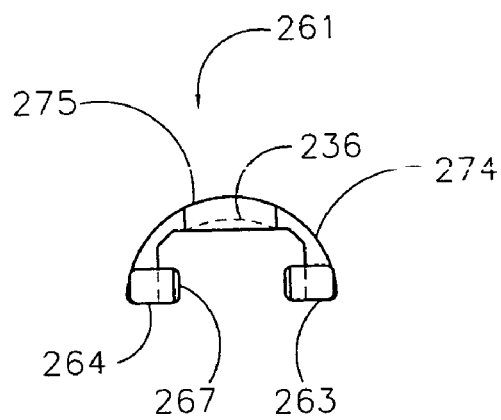
FIG. 17 is an end view of the vas engagement jaw of FIG. 15.
Figure 18:
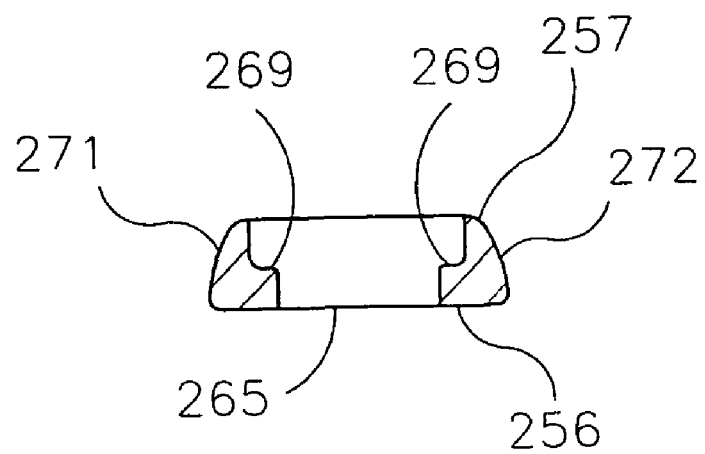
FIG. 18 is a section view of the vas engagement jaw of FIG. 15.
Figure 19:
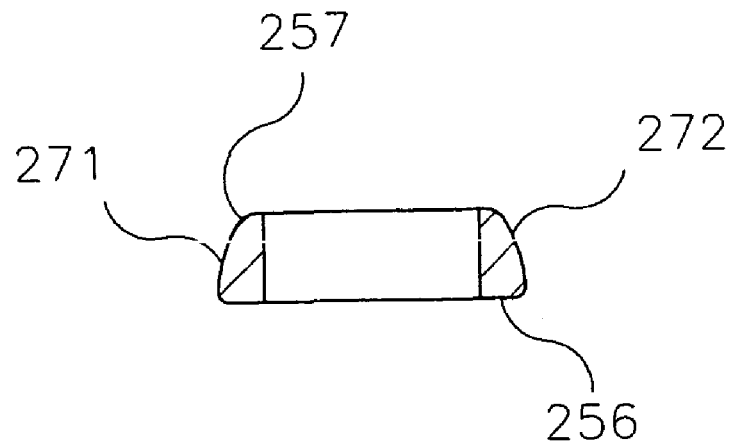
FIG. 19 is a section view of the vas engagement jaw of FIG. 15.

The clip 10a is then pushed further in the distal direction so that the arcuate portions 17, 18 of the clip 10a engage and slide along the support shelves 269 of the upper and lower jaws 261, 262 until the position illustrated in FIG. 14 is reached. FIG. 14 illustrates the position of the clip 10a as it just reaches the point where its arcuate portions 17, 18 are no longer held apart by the support shelves 269 and the arcuate portions 17, 18 are in registration with the ejection opening 255. The biasing force of the spring 30 then causes the arcuate portions 17, 18 to pass through the ejection opening 255 toward one another, and the biased occluding members 28, 29 to engage and occlude the vas.

The configuration shown in FIG. 14 is reached upon the trigger 211 reaching its full activation point (i.e., has been rotated to its proximal most position relative to the handgrip 212). In this configuration, the jaw push tube 238 is in contact with the distal side of jaw engagement grooves 236, and jaws 261 and 262 are pivoted about axis 234 to the engagement or closed position. The clip pusher 250 has advanced all three clips 10a, 10b, 10c distally one clip length. Upon ejection of the distal-most clip 10a, the remaining clips 10b, 10c remain in engagement with each other, the proximal pusher 253 and the clip pusher 250.

Upon release of trigger 211, the energy stored in the reset spring 224 causes the process to reverse. The main actuator link 214, sub-actuator 215, and jaws 261, 262 return to the reset or home position of FIG. 10. The applicator 200 is now ready for the delivery of the second clip 10b. Upon ejection of the final clip 10, the proximal pusher 253 is left at the distal end of the clip holder 233.

From the perspective of the user, the triggered actions of the applicator 200 appear to be simultaneous. The user places the open jaws 261, 262 over the portion of the fallopian tube to be occluded and squeezes the trigger 211 to its fullest extent in one continuous motion. This causes the jaws 261, 262 to close and engage the fallopian tube and a clip 10 to be pushed out of the tube assembly 230 and along the clip slot 265 to the ejection opening 266 where the clip 10 is released to engage and occlude the fallopian tube. Upon release of the trigger 211, the applicator 200 is immediately ready to apply another clip 10.

Another aspect of the invention provides methods of occluding a fallopian tube of a patient using occlusion clips and an applicator as described above. Because they involve the use of laparoscopic procedures using 3 mm instruments, these methods do not require the use of general anesthesia and involve relatively short recovery times. It should be noted that the occlusion procedure can be interval or post partum.

Figure 21:
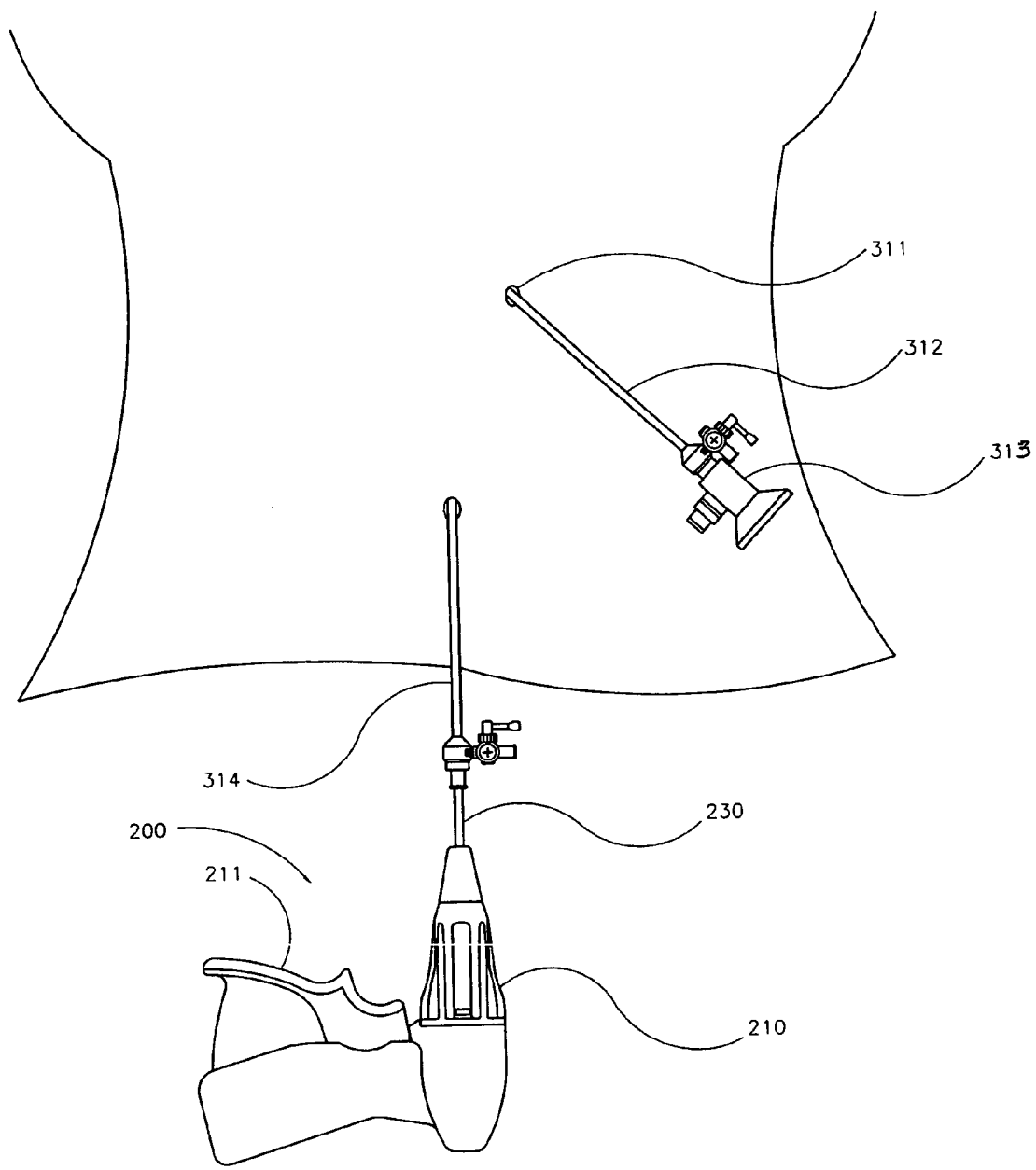
FIG. 21 is a perspective view of a portion of a patient's torso illustrating the positioning of instruments in a method according to an embodiment of the invention.

In an illustrative method according to the invention, a first trocar port 312 may be inserted into the abdominal cavity through the patient's umbilicus 311 as shown in FIG. 21. The first trocar port 312 may be sized to accept a 3 mm diameter laparoscope equipped with an endoscopic camera for ease of viewing the surgical field. A second trocar port 314 may then be inserted just below the umbilicus 311. The second trocar port 314 is sized to accommodate the insertion of the 3 mm jaw assembly 260 and tube assembly 230 of the occlusion clip applicator 200 described above.

After insertion of the first and second trocar ports 312, 314, the patient's abdomen is insufflated, using methods well know in the prior art. A laparoscope 313 is then inserted into the first trocar port 312 and the jaw assembly 260 and the distal end of the tube assembly 230 of a clip-loaded applicator 200 are inserted into the patient's abdominal cavity through the second trocar port 314.

The surgeon can then use the laparoscope 313 to locate the fallopian tube to be occluded and to guide the manipulation of the tube assembly 230 of the clip applicator 200. In this way, the surgeon can manipulate the jaw assembly 260 so that the jaws 261, 262 are positioned around a precise location along the length of the fallopian tube. This will typically be in the vicinity of the narrow portion, or isthmus, of the fallopian tube. With the clip applicator 200 in the initial configuration shown in FIG. 10, the surgeon positions the open jaws 261, 262 so that the fallopian tube is bracketed therebetween. The trigger 211 is then squeezed in a continuous motion as previously described to eject a clip 10 from the applicator 200. The trigger 211 is then released to return the applicator to the initial (reset) configuration. If desired, the procedure may be repeated for a second fallopian tube without relocation of the cannulas 312, 314.

Optionally, prior to clip placement, the area of the fallopian tube where the occlusion clip 10 is placed can be sprayed with a topical analgesic such as Bupivacaine or Marcaine.

The above procedure may be extended to include the placement of a second clip 10 on the fallopian tube. In this embodiment of the method, after ejection and placement of a first clip 10, the surgeon repositions the jaws 261, 262 of the applicator 200, which is in the reset configuration to another location along the fallopian tube, re-engages the fallopian tube with the jaws 261, 262 and ejects a second clip 10 by squeezing the trigger 211 of the applicator 200. The positions of the two occlusion clips may be anywhere along the fallopian tube but advantageously are both placed in the vicinity of the isthmus of the fallopian tube 17. Particularly advantageously, the two clips are spaced 5-10 mm apart.

In another extension of the above method, the additional step of severing the fallopian tube between the two occlusion clips may be accomplished.

In an alternate method of occluding a fallopian tube according to the invention, a laparoscope with a working channel is inserted into one trocar port. The laparoscope with a working channel is sized and configured to accept the tube assembly 230 of the clip applicator 200. The visualization cannula preferably has an overall diameter of 10 mm or less. The single visualization cannula may be inserted through one trocar port that is inserted into the patient's umbilicus. The method is similar to that described above except that only one trocar port need be inserted into the patient's abdominal cavity. Once the laparoscope is installed into the trocar port and the cavity insufflated, the tube assembly 230 of the clip applicator 200 may be inserted. The method may then proceed in the manners described above.

Many embodiments and adaptations of the present invention other than those herein described, will be apparent to those skilled in the art by the foregoing description thereof, without departing from the substance or scope of the invention. While the present invention has been described herein in detail in relation to its exemplary embodiments, it is to be understood that this disclosure is only illustrative and exemplary of the present invention. Accordingly, the foregoing disclosure is not intended to limit the scope of the present invention which is defined by the claims and their equivalents.

What is claimed is:

1. An occlusion clip applicator comprising:
   a jaw push tube having proximal and distal push tube ends and a jaw push tube interior;
   an elongate clip holder formed as a channel having first and second support rails attached thereto, the first and second support rails being substantially parallel and in alignment with each other, the clip holder having proximal and distal clip holder ends and being disposed inside the jaw push tube interior;
   a clip pusher having an elongate support member with a plurality of clip push fingers attached to the elongate support member, the elongate support member being mounted such that at least a portion of each clip push finger extends into the channel interior;
   a trigger; and
   a pair of jaws, each jaw having:
      proximal and distal jaw ends,
      an inner engaging side and an opposite outer side,
      a clip slot formed through the jaw from the inner engaging side to the outer side and extending distally from and through the proximal jaw end,
      a pair of parallel support shelves bounding at least a portion of the clip slot, the support shelves each having an outer surface facing away from the inner engaging side of the jaw; and
      a pair of ramps bounding a proximal portion of the clip slot, each ramp having a proximal end, wherein the proximal ends of the ramps have outer surfaces that match and are aligned with the respective support rails of the clip holder and are continuous with the outer surfaces of the respective support shelves;
   wherein the jaws are:
      pivotably mounted at their proximal ends to the distal clip holder end; and
      configured for engagement by the distal tube end for selective rotation between a fully open position and a closed position in which the engaging sides of the jaws are in contact with each other; and
      wherein the trigger is operably linked to the jaw push tube and to the clip pusher such that the trigger sequentially actuates first the jaw push tube and afterward the clip pusher, so that the applicator applies a first force in which the jaw push tube advances and causes the jaws to engage but the clip pusher does not move, and a second, later, force in which the clip pusher advances to urge a clip onto the support shelves of the engaged jaws.

2. An occlusion clip applicator according to claim 1 wherein the clip slot terminates in an ejection opening adjacent the distal jaw end, the clip slot having a slot width and the ejection opening having an ejection opening width that is greater than the slot width.

3. An occlusion clip applicator according to claim 1 wherein the support rails define a gap between the support rails, the gap being sized so that a first portion of an occlusion clip is narrower than the gap and so that a second portion of the occlusion clip is wider than the gap thus allowing the clip to be slidably disposed in the clip holder with the second portion of the clip engaging the support rails.

4. An occlusion clip applicator according to claim 3 wherein the clip push fingers each terminate in a clip engagement foot configured to engage a third portion of the occlusion clip so that distal movement of the clip pusher causes the occlusion clip to slide distally along the support rails.

5. An occlusion clip applicator according to claim 1 further comprising:
   means for selectively moving the jaw push tube in a distal direction to engage the jaws and cause them to rotate from the open position to the closed position; and
   means for selectively moving the clip pusher in the distal direction to cause distal movement of at least one occlusion clip disposed in the clip holder.

6. An occlusion clip applicator according to claim 5 wherein the means for selectively moving the jaw push tube and the means for selectively moving the clip pusher are adapted for moving the jaw push tube and the clip pusher in a predetermined sequence initiated by a user.

7. An occlusion clip applicator according to claim 1 further comprising:
   an actuator operatively associated with the jaw push tube and the clip pusher and configured to produce selective distal and proximal movement of the jaw push tube and the clip pusher relative to the clip holder.

8. An occlusion clip applicator according to claim 7 wherein the actuator is adapted to produce the distal movement of the jaw push tube and the clip pusher in a predetermined sequence initiated by a user.

9. An occlusion clip applicator according to claim 7 further comprising:
   a tube housing defining a tube chamber, the proximal push tube end, the proximal clip holder end and at least a portion of the actuator being disposed in the tube chamber.

10. An occlusion clip applicator according to claim 9 further comprising:
    a handle assembly attached to the tube housing, the handle assembly having a handgrip with a handgrip interior space and a trigger rotatably mounted to the handgrip, the trigger being operatively associated with the actuator for selective activation thereof.

11. An occlusion clip applicator for storing and applying a plurality of occlusion clips each having an upper occlusion member, a lower occlusion member, and a torsion spring connecting a proximal end of the lower occlusion arm to a proximal end of the upper occlusion arm, the upper and lower occlusion members defining a main body of the clip, having a maximum main body width, and a distal portion of the clip, having a maximum distal portion width greater than the maximum main body width, the torsion spring providing a pivot axis for rotational separation of the upper occlusion member and the lower occlusion member and providing a biasing force to bias the occlusion clip toward a closed configuration, the applicator comprising:
    a jaw push tube having proximal and distal push tube ends and a jaw push tube interior;
    an elongate clip holder configured to hold the plurality of occlusion clips, the clip holder being formed as a channel having first and second support rails attached thereto, the first and second support rails being substantially parallel and in alignment with each other and defining a gap with a gap width dimension that is greater than the main body width of the occlusion clips and less than the maximum distal portion width of the occlusion clips, the clip holder having proximal and distal clip holder ends and being disposed inside the jaw push tube interior;

a clip pusher having an elongate support member with a plurality of clip push fingers attached to the elongate support member, the elongate support member being mounted such that at least a portion of each clip push finger extends into the channel interior;

a trigger; and a pair of jaws, each jaw having:

proximal and distal jaw ends, an inner engaging side and an opposite outer side, a clip slot formed through the jaw from the inner engaging side to the outer side and extending distally from and through the proximal jaw end, a pair of parallel support shelves bounding at least a portion of the clip slot, the support shelves each having an outer surface facing away from the inner engaging side of the jaw; and a pair of ramps bounding a proximal portion of the clip slot, each ramp having a proximal end, wherein the proximal ends of the ramps have outer surfaces that match and are aligned with the respective support rails of the clip holder and are continuous with the outer surfaces of the respective support shelves;

wherein the jaws are:

pivotably mounted at their proximal ends to the distal clip holder end; and configured for engagement by the distal tube end for selective rotation between a fully open position and a closed position in which the engaging sides of the jaws are in contact with each other;

wherein the trigger is operably linked to the jaw push tube and to the clip pusher such that the trigger sequentially actuates first the jaw push tube and afterward the clip pusher, so that the applicator applies a first force in which the jaw push tube advances and causes the jaws to engage but the clip pusher does not move, and a second, later, force in which the clip pusher advances to urge a clip onto the support shelves of the engaged jaws; and wherein the clip slot has a width dimension that is greater than the maximum main body width of the occlusion clips and less than the maximum distal portion width of the occlusion clips.

12. An occlusion clip applicator according to claim 11 wherein the clip slot terminates in an ejection opening adjacent the distal jaw end, the ejection opening having an ejection opening width that is greater than the maximum distal portion width of the occlusion clips.

13. An occlusion clip applicator according to claim 11 wherein the clip push fingers each terminate in a clip engagement foot configured to engage the distal portions of the occlusion clips so that distal movement of the clip pusher causes the occlusion clips to slide distally along the support rails.

14. An occlusion clip applicator according to claim 11 further comprising:

means for selectively moving the jaw push tube in a distal direction to engage the jaws and cause them to rotate from the open position to the closed position; and means for selectively moving the clip pusher in the distal direction to cause distal movement of at least one occlusion clip disposed in the clip holder.

15. An occlusion clip applicator according to claim 14 wherein the means for selectively moving the jaw push tube and the means for selectively moving the clip pusher are adapted for moving the jaw push tube and the clip pusher in a predetermined sequence initiated by a user.

16. An occlusion clip applicator according to claim 11 further comprising:

an actuator operatively associated with the jaw push tube and the clip pusher and configured to produce selective distal and proximal movement of the jaw push tube and the clip pusher relative to the clip holder.

17. An occlusion clip applicator according to claim 16 wherein the actuator is adapted to produce the distal movement of the jaw push tube and the clip pusher in a predetermined sequence initiated by a user.

18. An occlusion clip applicator according to claim 16 further comprising:

a tube housing defining a tube chamber, the proximal push tube end, the proximal clip holder end and at least a portion of the actuator being disposed in the tube chamber.

19. An occlusion clip applicator according to claim 18 further comprising:

a handle assembly attached to the tube housing, the handle assembly having a handgrip with a handgrip interior space and a trigger rotatably mounted to the handgrip, the trigger being operatively associated with the actuator for selective activation thereof.

20. An occlusion clip applicator according to claim 1 further comprising:

a handle assembly having a trigger and a handgrip with a handgrip interior space;

a tube housing attached to the handle assembly and defining a tube chamber in communication with the handgrip interior space, the tube chamber and the handgrip interior space combining to form an actuator space; and an actuator disposed in the actuator space, the actuator configured for engagement and selective actuation by the trigger.

21. An occlusion clip applicator according to claim 20 wherein the clip slot terminates in an ejection opening adjacent the distal jaw end, the clip slot having a slot width and the ejection opening having an ejection opening width that is greater than the slot width.

22. An occlusion clip applicator according to claim 20 wherein the support rails define a gap between the support rails, the gap being sized so that a first portion of an occlusion clip is narrower than the gap and so that a second portion of the occlusion clip is wider than the gap, thus allowing the clip to be slidably disposed in the clip holder with the second portion of the clip engaging the support rails.

23. An occlusion clip applicator according to claim 22 wherein the clip push fingers each terminate in a clip engagement foot configured to engage a third portion of the occlusion clip so that distal movement of the clip pusher causes the occlusion clip to slide distally along the support rails.

24. An occlusion clip applicator according to claim 3 wherein the clip push fingers each terminate in a clip engagement foot configured to engage the second portion of the occlusion clip so that distal movement of the clip pusher causes the occlusion clip to slide distally along the support rails.

25. An occlusion clip applicator according to claim 22 wherein the clip push fingers each terminate in a clip engagement foot configured to engage the second portion of the occlusion clip so that distal movement of the clip pusher causes the occlusion clip to slide distally along the support rails.

26. An occlusion clip applicator according to claim 1, wherein each jaw further has a pair of ramps bounding a proximal portion of the clip slot, the ramps having outer surfaces that are aligned with the respective support rails of the clip holder and are continuous with the outer surfaces of the respective support shelves.

27. An occlusion clip applicator according to claim 11, wherein each jaw further has a pair of ramps bounding a proximal portion of the clip slot, the ramps having outer surfaces that are aligned with the respective support rails of the clip holder and are continuous with the outer surfaces of the respective support shelves.

* * * * *